United States Defensive Publication [19] (H) [11] T995,002

Zeringue, Jr. et al. [43] Jun. 3, 1980

[54] PURIFICATION OF SUCROSE ESTERS OF FATTY ACIDS BY A METHOD OF ULTRAFILTRATION

[75] Inventors: Hampden J. Zeringue, Jr., Destrehan; Reuben O. Feuge, New Orleans, both of La.

[73] Assignee: The United States of America as represented by the Secretary of Agriculture, Washington, D.C.

[21] Appl. No.: 62,824

[22] Filed: Aug. 1, 1979

Related U.S. Application Data

[63] Continuation-in-part of Ser. No. 879,999, Feb. 22, 1978, abandoned.

[51] Int. Cl.[3] ..... B01D 13/00; C02H 1/44; C07H 13/02

[52] U.S. Cl. ..... 210/23 F; 210/500 M; 536/119

[57] ABSTRACT

A sucrose ester product mixture containing sucrose esters, glycerides and free fatty acids, all fatty acid groups having carbon chains of 2–22 carbon atoms, has been separated into a concentrated sucrose ester fraction and a concentrated glyceride-fatty acid fraction by ultrafiltration through a polysulfone, anisotropic, microporous, membrane which normally partitions solutes of a molecular weight above 10,000 from those below a molecular weight of 10,000.

5 Claims, No Sheets Drawing,

10 Pages Specification

The file of this unexamined application may be inspected and copies thereof may be purchased (849 O.G. 1221, Apr. 9, 1968).